US007655753B2

(12) United States Patent
Deonarain et al.

(10) Patent No.: US 7,655,753 B2
(45) Date of Patent: Feb. 2, 2010

(54) CONJUGATE

(75) Inventors: Mahendra Persaud Deonarain, Wallington (GB); Simon Stafford, Birtley (GB)

(73) Assignee: PhotoBiotics Limited (GB)

( * ) Notice: Subject to any disclaimer, the term of this patent is extended or adjusted under 35 U.S.C. 154(b) by 353 days.

(21) Appl. No.: 10/485,923

(22) PCT Filed: Aug. 16, 2002

(86) PCT No.: PCT/GB02/03813

§ 371 (c)(1),
(2), (4) Date: Feb. 5, 2004

(87) PCT Pub. No.: WO03/015825

PCT Pub. Date: Feb. 27, 2003

(65) Prior Publication Data

US 2005/0234222 A1    Oct. 20, 2005

(30) Foreign Application Priority Data

Aug. 16, 2001  (GB)  ................................. 0120022.9

(51) Int. Cl.
 *C07K 14/00*     (2006.01)
 *A61K 38/00*     (2006.01)
(52) U.S. Cl. ........................................ 530/350; 514/12
(58) Field of Classification Search ................. 530/350, 530/387.1
See application file for complete search history.

(56) References Cited

U.S. PATENT DOCUMENTS

| 4,671,958 | A  | * | 6/1987  | Rodwell et al. ............. 424/1.53 |
| 5,851,527 | A  | * | 12/1998 | Hansen ..................... 424/178.1 |
| 6,500,800 | B1 | * | 12/2002 | Sobolev et al. ................. 514/3 |
| 2002/0127224 | A1 | * | 9/2002  | Chen ........................ 424/130.1 |
| 2002/0137901 | A1 | * | 9/2002  | Cavanaugh .................. 530/400 |

FOREIGN PATENT DOCUMENTS

| EP | 0 359 347 | 3/1990 |
| WO | WO 93 07283 | 4/1993 |
| WO | WO 96 10038 | 4/1996 |
| WO | WO9730170 | * 8/1997 |
| WO | WO 98 39011 | 9/1998 |

OTHER PUBLICATIONS

Eberle et al. The Structure of ColE1 rop in solution. Journal of Biomolecular NMR. May 1991. vol. 1, pp. 71-82.*
Yang et al. .Crystal Structures of Two Mutants-(K206Q, H207E) of the N-lobe of Human Transferrin with Increased Affinity for Iron. Protein Science, 1998, 2000. 9:49-52.*
Mott et al. The Solution Structure of the F42A Mutant of Human Interleukin 2. The Journal of Molecular Biology. 1995. vol. 247, pp. 979-994.*
Katre et al. Chemical Modification of Recombinant Interleukin 2 by Polyethylene Glycol Increases its Potency in the Murine Meth A Sarcoma Model. Proceedings of the National Academies of Science, U.S.A. 1987., vol. 84, pp. 1487-1491.*
Summary of SCORE sequence search results. No date.*
Akhlynina, Tamara V. et al., "Nuclear Targeting of Chloride $e_6$ Enhances Its Photosensitizing Activity," The Journal of Biological Chemistry, vol. 272, No. 33, pp. 20328-20331 (1997).
Drakopoulou, Eugenia et al., "Engineering Novel Proteins by the Transfer of Active Sites to a Stable Natural Scaffold," Perspectives on Protein Engineering 1996 International Conference, Paper No. 24, 18 pages (1996).
Sobolev, Alexander S. et al., "Targeted intracellular delivery of photosensitizers," Progress in Biophysics & Molecular Biology, vol. 73, No. 1, pp. 51-90 (2000).

* cited by examiner

*Primary Examiner*—Suzanne M. Noakes
(74) *Attorney, Agent, or Firm*—Fish & Richardson P.C.

(57) ABSTRACT

The present invention relates to a polypeptide comprising at least one alpha-helix having synthetically attached thereto a plurality of therapeutic or diagnostic moieties, wherein said therapeutic or diagnostic moieties may be the same or different and are spatially oriented on the polypeptide so as to minimise interactions between said moieties. Further aspects of the invention relate to a pharmaceutical composition comprising the polypeptide; a polynucleotide sequence encoding the polypeptide; an expression vector comprising said polynucleotide sequence; and a host cell transformed with said expression vector. The invention also provides a method of treatment comprising administering to a subject in need thereof a therapeutically effective amount of said polypeptide.

24 Claims, 6 Drawing Sheets

| Targeting Ligands | Photosensitising Drug Carrier | Additional functions |
|---|---|---|
| Single-chain Fv | Alpha helix | Membrane-active peptide |
| Fab fragment | 2-helix Bundle/coil | |
| | 3-helix Bundle/coil | Organelle targeting sequence |
| F(ab)₂ fragment | 4-helix Bundle/coil | |
| Peptide ligand | Highly glycoslyated glycoprotein | |
| | KKGKKGRKGGRKGK<br>Poly-basic peptide | |
| | EGGDDEDGDEGGDED<br>Poly-acidic peptide | |
| | YGSGYGYSYGYYGS<br>Poly-hydroxyl peptide | |
| | CGCGCGCSCGGGGC<br>Poly-thiol peptide | |
| | AGGLLVGVLALLGGA<br>Hydrophobic peptide | |

Key
- Antibody domains
- ● N-acetyl glucosamine
- ▦ Mannose
- ◉ Glucose
- ■ Galactose
- ▲ Fucose
- △ Sialic acid

FIG. 1

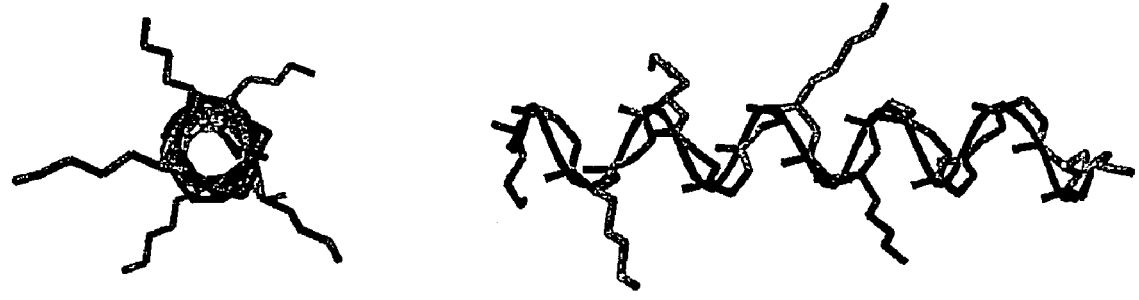
A            B
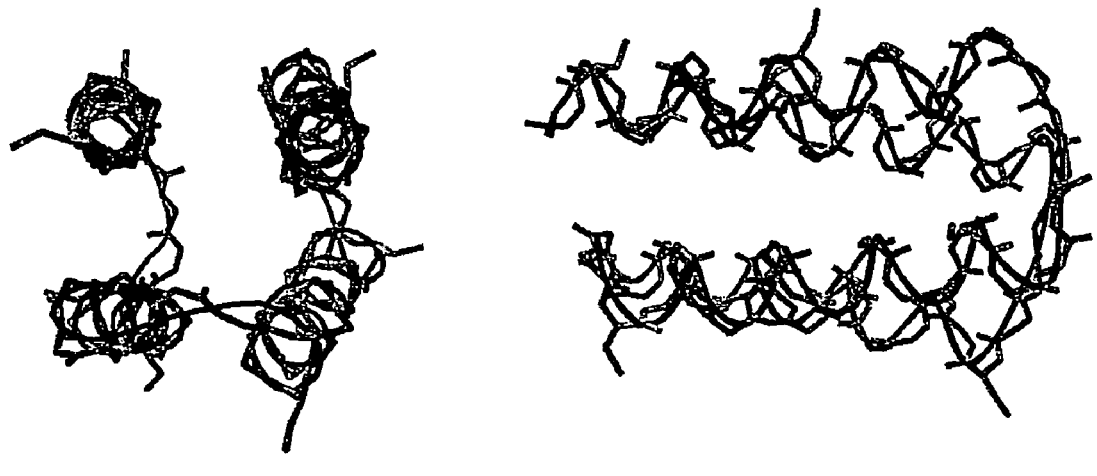
C            D
FIG. 2

SEQUENCE LISTING

<160> NUMBER OF SEQ ID NOS: 14

<210> SEQ ID NO 1
<211> LENGTH: 7
<212> TYPE: PRT
<213> ORGANISM: Artificial Sequence
<220> FEATURE:
<223> OTHER INFORMATION: SV 40 large T nuclear localisation

<400> SEQUENCE: 1

Lys Lys Lys Lys Arg Pro Arg
 1               5

<210> SEQ ID NO 2
<211> LENGTH: 17
<212> TYPE: PRT
<213> ORGANISM: Homo sapiens

-continued

<400> SEQUENCE: 2

Lys Arg Pro Met Asn Ala Phe Ile Val Trp Ser Arg Asp Gln Arg Arg
1 5 10 15

Lys

<210> SEQ ID NO 3
<211> LENGTH: 55
<212> TYPE: PRT
<213> ORGANISM: Artificial Sequence
<220> FEATURE:
<223> OTHER INFORMATION: ATP-binding protein N-terminal peptide containing mitochondria targeting

<400> SEQUENCE: 3

Met Leu Val His Leu Phe Arg Val Gly Ile Arg Gly Gly Pro Phe Pro
1 5 10 15

Gly Arg Leu Leu Pro Pro Leu Arg Phe Gln Thr Phe Ser Ala Val Arg
20 25 30

Tyr Ser Asp Gly Tyr Arg Ser Ser Ser Leu Leu Arg Ala Val Ala His
35 40 45

Leu Pro Ser Gln Leu Trp Ala
50 55

<210> SEQ ID NO 4
<211> LENGTH: 4
<212> TYPE: PRT
<213> ORGANISM: Artificial Sequence
<220> FEATURE:
<223> OTHER INFORMATION: Lysosomal membrane targeting

<400> SEQUENCE: 4

Lys Cys Pro Leu
1

<210> SEQ ID NO 5
<211> LENGTH: 4
<212> TYPE: PRT
<213> ORGANISM: Artificial Sequence
<220> FEATURE:
<223> OTHER INFORMATION: Endoplasmic reticulum (ER) Retention Signal

<400> SEQUENCE: 5

Lys Asp Glu Leu
1

<210> SEQ ID NO 6
<211> LENGTH: 23
<212> TYPE: PRT
<213> ORGANISM: Artificial Sequence
<220> FEATURE:
<223> OTHER INFORMATION: Influenza Haemaglutinin HA2

<400> SEQUENCE: 6

Gly Leu Phe Gly Ala Ile Ala Gly Phe Ile Glu Asn Gly Trp Glu Gly
1 5 10 15

Met Ile Asp Gly Trp Tyr Gly
20

<210> SEQ ID NO 7
<211> LENGTH: 18
<212> TYPE: PRT
<213> ORGANISM: Artificial Sequence
<220> FEATURE:

```
<223> OTHER INFORMATION: Polio virus vp1

<400> SEQUENCE: 7

Gly Ile Glu Asp Leu Ile Ser Glu Val Ala Gln Gly Ala Leu Thr Leu
 1               5                  10                  15

Val Pro

<210> SEQ ID NO 8
<211> LENGTH: 30
<212> TYPE: PRT
<213> ORGANISM: Homo sapiens

<400> SEQUENCE: 8

Ala Cys Tyr Cys Arg Ile Pro Ala Cys Ile Ala Gly Glu Arg Arg Tyr
 1               5                  10                  15

Gly Thr Cys Ile Tyr Gln Gly Arg Leu Trp Ala Phe Cys Cys
            20                  25                  30

<210> SEQ ID NO 9
<211> LENGTH: 29
<212> TYPE: PRT
<213> ORGANISM: Artificial Sequence
<220> FEATURE:
<223> OTHER INFORMATION: Sendai virus fusion protein F1

<400> SEQUENCE: 9

Phe Phe Gly Ala Val Ile Gly Thr Ile Ala Leu Gly Val Ala Thr Ser
 1               5                  10                  15

Ala Gln Ile Thr Ala Gly Ile Ala Leu Ala Glu Ala Arg
            20                  25

<210> SEQ ID NO 10
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 10

Lys Lys Gly Lys Lys Gly Arg Lys Gly Gly Arg Lys Gly Lys
 1               5                  10

<210> SEQ ID NO 11
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 11

Glu Gly Gly Asp Asp Glu Asp Gly Asp Glu Gly Gly Asp Glu Asp
 1               5                  10                  15

<210> SEQ ID NO 12
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 12

Tyr Gly Ser Gly Tyr Gly Tyr Ser Tyr Gly Tyr Tyr Gly Ser
 1               5                  10
```

```
<210> SEQ ID NO 13
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 13

Cys Gly Cys Gly Cys Gly Cys Ser Cys Gly Gly Gly Gly Cys
 1               5                  10

<210> SEQ ID NO 14
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 14

Ala Gly Gly Leu Leu Val Gly Val Leu Ala Leu Leu Gly Gly Ala
 1               5                  10                  15
```

CONJUGATE

CLAIM OF PRIORITY

This application claims priority under 35 U.S.C. §371 to PCT application Ser. No. PCT/GB02/03813, filed on Aug. 16, 2002, which claims priority to Application No. 0120022.9, filed Aug. 16, 2001, each of which is incorporated by reference in its entirety.

The present invention relates to the field of recombinant molecules that are capable of delivering therapeutic agents to target cells.

BACKGROUND TO INVENTION

Current treatment of disease is predominantly non-targeted. Drugs are administered systemically, e.g. orally, which exposes many other tissues as well as the tissues which are diseased. In cancer therapy, chemotherapeutic drugs are specific for cells which are growing and dividing rapidly, as they work mainly by a mechanism which interferes with DNA replication [1]. However, other cells may take up the drug and also become intoxicated, such as rapidly dividing bone marrow stem cells, resulting in immunosupression. In infectious diseases, anti-bacterial drugs are introduced into the blood (orally or by injection) and interfere with a particular bacterial metabolic pathway. Again, exposure to other tissues can result in side effects. Virally-infected cells are difficult to treat as their metabolism is nearly identical to uninfected cells.

It is widely acknowledged that the future of medicine lies in the tailoring of drugs to the disease. This means delivering the therapeutic agent to the correct target tissue, rather than the non-selective hit and miss approach of most of the conventional drug treatments used today. This approach may result in the administration of lower doses, lower side effects and toxicities and overall better responses. Advances in genomics may one day mean that drugs can be tailored to the individual, as one individual's cancer may differ from another's.

There are many drugs used clinically today that are effective at destroying or treating diseased cells, once they have accumulated in the correct tissue. The problem therefore lies with the specific targeting of drugs, rather than the effector mechanism. Examples of targeting include targeted ionising radiation as opposed to external beam radiotherapy [2], targeted chemotherapy drugs (e.g. methotrexate or doxorubicin) as opposed to free drugs [3] and toxins [4]. Photodynamic therapy (PDT) is a particularly good example as it is already well established in many treatments. However, it is becoming apparent that a better therapeutic outcome may result from pre-targeting a photosensitizing (PS) drug to the correct tissues in addition to targeting the light source, which is not accurate at a cellular level [5].

Targeting drugs or other effectors to the desired cells has been previously proposed. One of the main approaches to targeting is to use antibodies as the targeting element of a multifunctional molecule [6]. The ideal design for such a multifunctional molecule would be one which is highly specific for diseased cells, able to carry many drugs with high capacity without compromising their function, and able to deposit the drug in the sub-cellular compartment which would primarily be affected.

Antibody Targeting

Antibodies have naturally evolved to act as the first line of defence in the mammalian immune system. They are complex glycoproteins which have exquisite diversity and specificity. This diversity arises from programmed gene shuffling and targeted mutagenesis, resulting in probably a trillion different antibody sequences [7]. Consequently, this diversity means that antibodies can bind to practically any target molecule. It is now possible to mimic antibody selection and production in vitro, selecting for recombinant human antibodies against virtually any desired target [8]. A significant number of biotechnological drugs in development are based on antibody targeting [6]. The most popular in vitro selection technique is antibody phage display, where antibodies are displayed and manipulated on the surface of viruses [8]. There are many therapeutic antibodies being developed for a range of diseases, primarily cancer. Table 1 lists some of these antibodies.

Antibodies can bind with a high degree of specificity to target cells expressing the appropriate receptor. The affinity of an antibody is a measure of how well an antibody binds to the target (antigen). It is usually described by an equilibrium dissociation constant (Kd). Technology exists to select and manipulate antibodies which have the desired kinetic binding properties. For antibodies that need to be internalised, the association rate is more important, as the dissociation rate does not function if the antibody is taken into the cell.

As with all biological molecules, the size of the antibody affects its pharmacokinetics in vivo [12]. Larger molecules persist longer in the circulation due to slow clearance (large glycoproteins are cleared through specific uptake by the liver). For whole antibodies (molecular weight approx. 150 KDa) which recognise a cancer cell antigen in a mouse model system, 30-40% can be taken up by the tumour, but because they persist longer in the circulation, it takes 1-2 days for a tumour:blood ratio of more than one to be reached. Typical tumour:blood ratios are 5-10 by about day 3 [13]. With smaller fragments of antibodies, which have been produced by in vitro techniques and recombinant DNA technology, the clearance from the circulation is faster (molecules smaller that about 50 KDa are excreted through the kidneys, as well as the liver). Single-chain Fvs (about 30 KDa) are artificial binding molecules derived from whole antibodies, but contain the minimal part required to recognise antigen [14]. Again in mouse model systems, scFvs can deliver 1-2% of the injected dose, but with tumour:blood ratios better than 25:1, with some tumour:organ ratios even higher [15]. As scFvs have only been developed over the last 10 years, there are not many examples in late clinical trials. From clinical trials of whole antibodies, the amount actually delivered to tumours is about 0.1 to 1% of that seen in mouse models, but with similar tumour:organ ratios [16]. If another molecule is attached to the antibody, then the new size determines the altered pharmacokinetic properties. Other properties such as net charge and hydrophilicity have effects on the targeting kinetics [17].

Some cell surface antigens are static or very slowly internalise when bound by a ligand such as an antibody. There are some which have a function that requires internalisation, such as cell signalling or uptake of metals and lipids. Antibodies can be used to deliver agents intracellularly. These agents can be therapeutic—repairing or destroying diseased cells. Examples include gene delivery [18], the intracellular delivery of toxins (e.g. Pseudomonas exotoxin [4]), enzymes (e.g. ribonuclease [19]) and drugs (e.g. methotrexate [3]). Some of these agents need targeting to particular sub-cellular organelles in order to exert their effects. Advances in cell biology have uncovered 'codes'—amino acid sequences which direct intracellular proteins to certain sub-cellular compartments. There are specific sequences to target to the nucleus, endoplasmic reticulum, golgi, lysosomes and mitochondria (Table 2).

There has been much research into targetable therapeutic drugs where novel effector functions have been linked to antibodies or other targeting ligands. Some of these need to be internalised to successfully deliver a toxic agent. Many of these have shown good results in vitro and in vivo in animal models, but have been disappointing in the clinic. Immunotoxins have shown problems such as immune reactions and liver/kidney toxicity [25]. There have been developments with new 'humanised' immunotoxins based on enzymes such as ribonuclease [19] and deoxyribonuclease [26]. These potentially have lower side effects and are more tolerable, but still do not have a bystander killing effect. Chemotherapy drugs tend to be much less active when linked to proteins as they are not released effectively and radioimmunotherapy tends to irradiate other tissues en route to the tumour, giving rise to bone marrow and liver toxicity. Photosensitising (PS) drugs are particularly attractive agents to link to proteins, as the cytotoxic elements are the singlet oxygen species generated from them and not the PS drugs themselves [5].

Photodynamic Therapy (PDT)

Photodynamic therapy is a minimally invasive treatment for a range of conditions where diseased cells and tissues need to be removed [27]. Unlike ionising radiation, it can be administered repeatedly at the same site. Its use in cancer treatment is attractive because conventional modalities such as chemotherapy, radiotherapy or surgery do not preclude the use of PDT and vice versa. Photodynamic therapy is also finding other applications where specific cell populations must be destroyed, such as blood vessels (in age-related macular degeneration (AMD) or in cancer), the treatment of immune disorders, cardiovascular disease, and microbial infections. PDT is a two-step or binary process starting with the administration of the PS drug, by intravenous injection, or topical application for skin cancer. The physico-chemical nature of the drug causes it to be preferentially taken up by cancer cells or other target cells [28]. Once a favourable tumour (or other target): normal organ ratio is obtained, the second step is the activation of the PS drug with a specific dose of light, at a particular wavelength. This ultimately causes the conversion of molecular oxygen found in the cellular environment into reactive oxygen species (ROS) primarily singlet oxygen ($^1O_2$), although reactions of intermediate photochemically produced species also generate hydroxyl radicals (OH.) and superoxide ($O_2^-$.). These molecular species cause damage to cellular components such as DNA, proteins and lipids [29]. PDT is a cold photochemical reaction, i.e. the laser light used is not ionising and the PS drugs have very low systemic toxicity. The combination of PS drug and light result in low morbidity and insignificant functional disturbance and offers many advantages in the treatment of diseases. There is growing evidence that PDT response rates and durability of responses are as good as or even superior to standard locoregional therapies [27].

The light activation of ROS is highly cytotoxic. In fact some natural processes in the immune system utilise ROS as a way of destroying unwanted cells. These species have a short lifetime (<0.04 μs) and act over a short radius (<0.04 μm) from their point of origin. The destruction of cells leads to a necrotic area of tissue which eventually sloughs away or is resorbed. The remaining tissue heals naturally, usually without scarring. There is no tissue heating and connective tissue such as collagen and elastin are unaffected, resulting in less risk to the underlying structures compared to thermal laser techniques, surgery or external beam radiotherapy. More detailed research has shown that PDT induces apoptosis (non-inflammatory cell death), and the resulting necrosis (inflammatory cell lysis) seen is due to the mass of dying cells which are not cleared away by the immune system [30].

Generally PS drugs are administered systemically, with some topical applications for skin lesions. When the PS drug has accumulated in the target tissue, with ratios typically 2-5:1 compared with normal surrounding tissues (except in the brain where the ratio can be up to 50:1), low power light of a particular wavelength is directed onto the tumour (or the eye in AMD treatment [31]). Because human tissue can transmit light most effectively in the red region of the visible light spectrum, PS drugs which can absorb red light (630 nm or above) can be activated up to a depth of about 1 cm. Patients must avoid sunlight until systemically administered PS drugs clear from the body, otherwise they may have skin photosensitivity, resulting in skin burn.

The treatment scheme is attractive to the clinician in that superficial diseases can usually be treated with local anaesthesia and sedation. The generally low toxicity (with the possible exception of skin photosensitivity) limits the need for other medication. Topical treatments do not require sterile conditions and can be given in an outpatient clinic.

Research on a number of PS drugs including silicon phthalocyanines has shown that PDT induces apoptosis-programmed cell death [32]. Apoptosis is the highly orchestrated and evolutionary conserved form of cell death in which cells neatly commit suicide by chopping themselves into membrane-packaged pieces [33]. These apoptotic bodies are marked for phagocytosis by the immune system. Usually, too much apoptosis in a small area 'overloads' the immune system and the area eventually becomes necrotic, with inflammatory consequences.

Photofrin (porfimer sodium), 5-aminolaevulanic acid (ALA) and Verteporfin (BPD-benzoporphyrin derivative) are three PS drugs which have regulatory approval. A promising, potent second generation PS drug, Foscan (temoporfin; meta-tetrahydroxyphenyl chlorin) is encountering problems in acquiring approval from the FDA and MCA. Porfimer sodium, the first PS drug to be approved, is licensed for use in bladder, stomach, oesophagus, cervix and lung cancer. Its performance is moderate due to poor light absorption characteristics in the red end of the spectrum (activated at 630 nm), meaning it can only penetrate about 5 mm into tissues. It also persists in the body for weeks, leading to skin photosensitivity. However it has been effective in the treatment of the above cancers [27]. ALA is applied topically in the treatment of skin lesions and is converted endogenously to protoporphyrin IX, a naturally-occurring PS molecule. This can be activated at many wavelengths and its depth of effect is less than 2 mm. 'Visudyne' (Verteporfin) also performs well in AMD [31], without the issues of tissue penetration found in tumour applications.

The newer generation of PS drugs have longer activation wavelengths thus allowing deeper tissue penetration by red light, higher quantum yield and better pharmacokinetics in terms of tumour selectivity and residual skin photosensitivity. These classes of PS drugs include the phthalocyanines, chlorins, texaphyrins and purpurins. The synthetic chlorin, Foscan is a very potent PS drug with a wavelength of activation of 652 nm, good quantum yield of singlet oxygen and skin photosensitivity of about 2 weeks. There have been many clinical trials for a variety of cancers, with good results [27]. There are other PS drugs which have been developed and are in trials which can adsorb at 740 nm, such as meso-tetrahydrophenyl bacteriochlorin (m-THPBC).

Clinical PDT

PDT can achieve disease control rates similar to conventional techniques with lower morbidity rates, simplicity of use and improved functional and cosmetic outcome. PDT has mainly been used where conventional approaches have failed or are unsuitable. These include pre-malignant dysplastic lesions and non-invasive cancers which are commonly found in the mucosa of aerodigestive and urinary tracts (e.g. oral cavity, oesophagus and bladder). Current treatments for cancer at this stage are not very successful and good responses here would prevent larger solid tumours or metastatic spreads occurring. Treatment for Barrett's oesophagus usually involves an oesophagectomy, which requires general anaesthesia, has a risk of morbidity and loss of function and disfigurement. PDT is being seen as an attractive option because of the large area which can be treated superficially with less risk. Photofrin, ALA and Foscan have produced good responses in these types of cancers in clinical trials (Table 3).

Due to easy light accessibility, the treatment of cutaneous disease such as skin cancer has produced good results with systemic and topical PS drugs (Table 3). Head, neck and oral lesions have also produced good results and are well suited due to the good cosmetic outcome of the treatment (Table 3). Treatment of other cancers are being tested as advances are being made in laser and light delivery technology. Endoscopes can be used to deliver the activating light dose to any hollow structure such as the oesophagus and bronchial cavity, thus expanding the treatment range to gastrointestinal and lung cancers (Table 3) with minimal surgery. Large areas such as the pleura and peritoneum can be treated, where radiotherapy would not be able to give a high enough curative dose. PDT has great promise in the treatment of these surface serosal cancers, in combination with debulking surgery. Light can be delivered to these large surfaces in a short time, through hollow cavities. The limited depth of activity would be an advantage, as the critical underlying organs would be spared (Table 3). Adjuvant therapy is also an option being investigated, where the solid tumour is surgically removed and any remaining tumour cells are destroyed by one round of PDT in the cavity formed.

Although surface cancers may be the most amenable to PDT, solid tumours may also be able to undergo interstitial treatment, where the PS drug is administered systemically or by intra-tumour injection, followed by the insertion of laser fibres through needles equally spread throughout the tumour. This can result in necrosis of very large tumours (Table 3).

To summarise, there are several advantages of PDT therapy. It offers non-invasive, low toxicity treatments which can be targeted by the light activation. The target cells cannot develop resistance to the cytotoxic species (ROS). Following treatment, little tissue scarring exists. However, PS drugs are not very selective for the target cells with target:blood ratios typically in single figures. Because PS drugs "piggy-back" on blood proteins, they persist longer in the circulation than is desired, leaving the patient photosensitive for 2 weeks in the best of cases. It is becoming increasingly clear that PS drugs need to accumulate inside cells as the generated ROS have a short pathlength. This may not be achieved effectively with current PS drugs.

Targetable PDT

Photosensitiser drugs can still be active and functional while attached to carriers, as the cytotoxic effect is a secondary effect resulting from light activation. This makes them very amenable to specific drug delivery mechanisms. Currently, the approaches used to link PS drugs to targetable elements include direct conjugation of derivatised PS drugs to whole monoclonal antibodies or other ligands [34-37]. However, this often results in a heterogeneous mixture of antibody-PS drug molecules as the chemistry is not accurate. Whole antibodies have a molecular weight of 150 KDa, resulting in very large immunoconjugates with unfavourable pharmacokinetics, such as poor tumour:organ ratios [36] which take a long time to achieve. It is also likely that PS drugs linked to large adjacent residues of a protein can have a detrimental effect on PS photophysics, with quenching of the desired PS excited states occurring due to adverse PS-protein interactions. The non-specific attachment of PS drugs onto antibodies or other ligands can result in a severe compromise in binding ability of the ligand. The antibody binding site may be hindered by such reactions, dramatically lowering the affinity and specificity of the antibody. Too many PS drugs attached can also affect the hydrophobicity of a protein and may have an adverse effect on the structure and pharmacokinetics [36].

Some researchers have tried to circumvent these problems by attempting to link PS drugs to designated 'carriers' such as chemically synthesised branched carbohydrate chains and poly-lysine chains. These approaches all require additional conjugation steps as the ligand-carriers cannot be made entirely recombinantly. Using chains of pure poly-lysine may also give rise to problems, for example, proteolyic instability in vivo, or the concentration of hydrophobic PS drugs in one part of the molecule leading to aggregation and quenching of adjacent PS drugs-excited states.

The present invention seeks to alleviate some of the above-mentioned problems of the prior art, thereby providing an improved system for targeting and delivery of therapeutic and/or diagnostic agents.

STATEMENT OF INVENTION

In a first aspect, the present invention provides a polypeptide comprising at least one alpha-helix having synthetically attached thereto a plurality of therapeutic or diagnostic moieties, wherein said therapeutic or diagnostic moieties may be the same or different and are spatially oriented on the polypeptide so as to minimise interactions between said moieties.

A second aspect relates to the use of a polypeptide according to the invention in the preparation of a medicament for the prevention and/or treatment of disease.

A third aspect relates to a polynucleotide sequence encoding all or part of the polypeptide of the invention.

A fourth aspect relates to an expression vector comprising the polynucleotide sequence of the invention.

A fifth aspect relates to a host cell transformed with the expression vector or the polynucleotide sequence of the invention.

A sixth aspect relates to a method for preparing a polypeptide according to the invention comprising expressing the polynucleotide of the invention, or culturing the host cell of the invention under conditions which provide for expression of the polypeptide.

A seventh aspect relates to a method of transporting a therapeutic or diagnostic agent into a cell comprising exposing a cell to a polypeptide according to the invention.

An eighth aspect relates to a pharmaceutical composition comprising a polypeptide according to the invention and a pharmaceutically acceptable diluent, excipient or carrier.

A ninth aspect relates to a method of treatment comprising administering to a subject in need thereof a therapeutically effective amount of a polypeptide according to the invention.

A tenth aspect relates to a diagnostic method comprising administering to a subject a diagnostically effective amount of a polypeptide according to the invention.

An eleventh aspect relates to a method of preparing a polypeptide according to the invention, said method comprising conjugating a therapeutic or diagnostic agent to an alpha-helical polypeptide.

DETAILED DESCRIPTION

Various preferred features and embodiments of the invention are described below.

As mentioned above, a first aspect of the present invention provides a polypeptide comprising at least one alpha-helix having synthetically attached thereto a plurality of therapeutic or diagnostic moieties, wherein said therapeutic or diagnostic moieties may be the same or different and are spatially oriented on the polypeptide so as to minimise interactions between said moieties.

Preferably, said therapeutic or diagnostic moieties are spatially oriented on the polypeptide so as to minimise unfavourable or disruptive interactions between said moieties.

Typically, the polypeptide may be a conjugate, for example, a protein conjugate, i.e., a fusion protein.

Preferably, the polypeptide of the invention comprises one or more specific amino acid residues for the purpose of site-specific conjugation to said therapeutic or diagnostic moieties.

In one preferred embodiment, said specific amino acid residues comprise one or more basic amino acids.

In one preferred embodiment, said specific amino acid residues comprise one or more acidic amino acids.

In another preferred embodiment, said specific amino acid residues comprise one or more hydroxyl-containing amino acids.

In another preferred embodiment, said specific amino acid residues comprise one or more thiol-containing amino acids.

In another preferred embodiment, said specific amino acid residues comprise one or more hydrophobic amino acids. By way of definition, the term "hydrophobic amino acid residue" encompasses amino acids having aliphatic side chains, for example, valine, leucine and isoleucine.

In a particularly preferred embodiment of the invention, the alpha-helix comprises at least two functional amino acid residues positioned so as to protrude externally from said alpha-helix so that each functional amino acid residue does not hinder another. Preferably, the functional amino acid residues are suitable for cross-linking to one or more therapeutic or diagnostic agents. Examples of such functional amino acids include lysine, cysteine, threonine, serine, arginine, glutamate, aspartate, tyrosine.

Typically, the α-helix is proteolytically and temperature stable, and is designed so that functional groups from one type of side chain (e.g. basic residues such as lysine and arginine) protrude from the helix in such a way that each functional group is spatially separated from each other.

The length of the helical peptide may be varied to incorporate more or fewer functional amino acid residues, thereby accommodating more or fewer therapeutic agents respectively, as required. Likewise, the position and number of functional amino acid residues can be altered to increase or decrease the distance between the attached therapeutic agents, or to vary the number of therapeutic agents attached. In each case, the spatial arrangement of the functional amino acid residues is such that there is little or no interference between the therapeutic agents attached thereto.

Preferably, the alpha-helix is a 19-residue helix with functional amino acid residues at positions 2, 8, 10, 14 and 16.

By way of example, and as illustrated in FIG. 2A, the polypeptide may comprise a 19-residue peptide helix with functional amino acids such as lysine or arginine residues at positions 2, 8, 10, 14, 16. This results in an approximately equal number of positively charged residues above/below or either side of the helical axis (viewed in FIG. 2B). These positively charged residues can be seen to be spatially separated when the helix is viewed 'end on' (FIG. 2A).

Preferably, the side-chain type is the same for any one helix.

In one preferred embodiment, the polypeptide of the invention may comprise two or more alpha-helical polypeptides in the form of a multi-helix bundle. Such multi-helix bundles enable the attachment of a greater number of therapeutic agents. Furthermore, without wishing to be bound by theory, it is believed that multi-helix bundles of this type may exhibit an improved stability over the corresponding single alpha-helical polypeptides.

In one preferred embodiment, the polypeptide of the invention comprises two alpha-helices, i.e., a two-helix bundle. These can be of a single-chain or separate chain format.

In another preferred embodiment, the polypeptide of the invention comprises three alpha-helices, i.e., a three-helix bundle. Again, these can be of a single-chain or separate chain format.

In another preferred embodiment, the polypeptide of the invention comprises four alpha-helices, i.e., a four-helix bundle. Again, these can be of a single-chain or separate chain format. By way of example, a four-helix bundle is, shown in FIGS. 2C and 2D. This example shows a 4-helix bundle with engineered cysteine residues for thiol coupling. Eight thiols are available for coupling which result in optimal spacing of the therapeutic agents when viewed from 'end on' (FIG. 2C) and from the side (FIG. 2D).

Preferably, the polypeptide of the invention comprises a natural or synthetic four helix bundle.

In one especially preferred embodiment, the polypeptide of the invention is the wild-type or mutant form of 'rop' (repressor of primer).

More preferably still, the polypeptide of the invention is a derivative of wild-type or mutant form of 'rop' comprising cysteine or lysine residues at optimal positions in the helix bundle.

Preferably, the polypeptide is scFv4-helix bundle-cys or scFv4-helix bundle-lys.

Targeting Element

In one particularly preferred embodiment of the invention, the polypeptide further comprises a targeting element.

Preferably, the polypeptide of the invention is in the form of a fusion protein. Thus, polypeptides according to the invention may include fusion proteins in which a targeting protein is linked to the alpha helix bearing a plurality of therapeutic or diagnostic agents via their polypeptide backbones through genetic expression of a DNA molecule encoding these proteins, directly synthesised proteins, and coupled proteins in which pre-formed sequences are associated by a cross-linking agent.

Preferably, the targeting element is selected from a recombinant antibody, a Fab fragment, a F(ab')$_2$ fragment, a single chain Fv, a diabody, a disulfide linked Fv, a single antibody domain and a CDR.

As used herein, the term "CDR" or "complementary determining region" refers to the hypervariable regions of an antibody molecule, consisting of three loops from the heavy chain and three from the light chain, that together form the antigen-binding site.

By way of example, the antibody may be selected from Herceptin, Rituxan, Theragyn (Pemtumomab), Infliximab, Zenapex, Panorex, Vitaxin, Protovir, EGFR1 or MFE-23.

In one preferred embodiment, the targeting element is a genetically engineered fragment selected from a Fab fragment, a F(ab')$_2$ fragment, a single chain Fv, or any other antibody-derived format.

Conventionally, the term "Fab fragment" refers to a protein fragment obtained (together with Fe and Fc' fragments) by papain hydrolysis of an immunoglobulin molecule. It consists of one intact light chain linked by a disulfide bond to the N-terminal part of the contiguous heavy chain (the Fd fragment). Two Fab fragments are obtained from each immunoglobulin molecule, each fragment containing one binding site. In the context of the present invention, the Fab fragment may be prepared by gene expression of the relevant DNA sequences.

Conventionally, the term "F(ab')$_2$" fragment refers to a protein fragment obtained (together with the pFc' fragment) by pepsin hydrolysis of an immunoglobulin molecule. It consists of that part of the immunoglobulin molecule N-terminal to the site of pepsin attack and contains both Fab fragments held together by disulfide bonds in a short section of the Fc fragment (the hinge region). One F(ab')$_2$ fragment is obtained from each immunoglobulin molecule; it contains two antigen binding sites, but not the site for complement fixation. In the context of the present invention, the F(ab')$_2$ fragment may be prepared by gene expression of the relevant DNA sequences.

As used herein, the term "Fv fragment" refers to the N-terminal part of the Fab fragment of an immunoglobulin molecule, consisting of the variable portions of one light chain and one heavy chain. Single-chain Fvs (about 30 KDa) are artificial binding molecules derived from whole antibodies, but which contain the minimal part required to recognise antigen.

In another preferred embodiment, the targeting element is a synthetic or natural peptide, a growth factor, a hormone, a peptide ligand, a carbohydrate or a lipid.

The targeting element can be designed or selected from a combinatorial library to bind with high affinity and specificity to the target antigen. Typical affinities are in the $10^{-6}$ to $10^{-15}$ M $K_d$ range. Functional amino acid residues, present in the targeting element, which could participate in the therapeutic agent attachment reaction may be altered by site-directed mutagenesis where possible, without altering the properties of the targeting element. Examples of such changes include mutating any free surface thiol-containing residues (cysteine) to serines or alanines, altering lysines and arginines to asparagines and histidines, and altering serines to alanines.

The target cells themselves can be human, other mammalian cells or microbial cells (e.g. anti-bacterial PDT using anti-bacterial antibodies [39]).

As discussed above the targeting element and the polypeptide may be linked directly or indirectly via a linker moiety. Direct linkage may occur through any convenient functional group on one of the proteins, such as a hydroxy, carboxy or amino group. Indirect linkage will occur through a linking moiety. Suitable linking moieties include bi- and multi-functional alkyl, aryl, aralkyl or peptidic moieties, alkyl, aryl or aralkyl aldehydes acids esters and anyhdrides, sulphydryl or carboxyl groups, such as maleimido benzoic acid derivatives, maleimido proprionic acid derivatives and succinimido derivatives or may be derived from cyanuric bromide or chloride, carbonyldiimidazole, succinimidyl esters or sulphonic halides and the like. The functional groups on the linker moiety used to form covalent bonds between the alpha helix and targeting elements may be two or more of, e.g., amino, hydrazino, hydroxyl, thiol, maleimido, carbonyl, and carboxyl groups, etc. The linker moiety may include a short sequence of from 1 to 4 amino acid residues that optionally includes a cysteine residue through which the linker moiety bonds to the transport protein. Alternatively, the targeting element and the polypeptide may be linked by leucine zippers, dimerisation domains, or an avidin/biotin linker.

Additional Sequences

In an especially preferred embodiment of the invention, the polypeptide further comprises one or more additional sequences selected from a sub-cellular targeting peptide and a membrane active peptide. The additional amino acid sequence may be attached either to the targeting element or to the alpha helix of the polypeptide, or to both.

Examples of sub-cellular targeting peptides include nuclear localisation sequences (NLS), mitochondrial localisation sequences, lysosomal targeting peptides, endoplasmic reticulum retrieval signals, golgi targeting sequences. These sequences serve to deliver the therapeutic agent to certain subcellular compartments, particularly the nucleus. The additional sequences can also be membrane-active peptides (Table 2) which function to disrupt the endosomal compartment containing the fusion protein after internalisation. This will facilitate the release of the therapeutic agent into the cytosol of the cell where it can have a potent action.

In one particularly preferred embodiment, the sub-cellular targeting peptide targets the nucleus and comprises a sequence selected from KKKKRPR (SEQIDNO:1) and KRPMNAFIVWSRDQRRK (SEQIDNO:2).

In another particularly preferred embodiment, the sub-cellular targeting peptide targets the mitochondria and comprises the sequence MLVHLFRVGIRGGPFP GRLLPPLR-FQTFSAVRYSDGYRSSSLLRAVAHLPSQLWA (SEQIDNO:3).

In yet another particularly preferred embodiment, sub-cellular targeting peptide targets lysosomes and comprises the sequence KCPL (SEQIDNO:4).

In another particularly preferred embodiment, the sub-cellular targeting peptide allows proteins to traffic back to the endoplasmic reticulum and comprises the sequence KDEL (SEQIDNO:5).

In one especially preferred embodiment, the membrane active peptide targets the membrane and comprises a sequence selected from the following:

(i) GLFGAIAGFIENGWEGMIDGWYG(SEQIDNO:6);

(ii) GIEDLISEVAQGALTLVP(SEQIDNO:7);

(iii) ACYCRIPACIAGERRYGTCIYQGRLWAFCC (SEQIDNO:8); and (iv) FFGAVIGTIALGVATSAQITAGIALAEAR(SEQIDNO:9).

Glycosylated Peptides

In one preferred embodiment, the polypeptide comprises a protein having one or more N- or O-linked carbohydrate residues spatially oriented so as to minimise interactions between said carbohydrates or therapeutic or diagnostic moieties attached thereto.

Thus, in one preferred embodiment, the polypeptide comprises a glycosylated protein e.g. human serum albumin) or comprises a protein having one or more N- or O-linked glycosylation sites. By way of definition, the term "glycosylated protein" refers to a glycoprotein, i.e., a protein having one or more carbohydrates attached thereto. Typically, glycoproteins contain oligosaccharide units linked to either asparagine side chains by N-glycosidic bonds, or to serine and threonine side chains by O-glycosidic bonds. Accordingly, a protein having N- or O-linked glycosylation sites includes any protein containing amino acid residues having one or more OH or $NH_2$ side chains.

These proteins may be expressed in a eukaryotic system such as mammalian cells, yeasts or insect cells, to ensure full glycosylation. Derivatised therapeutic agents, whose chemistry is compatible with chemical attachment to hydroxyl or carboxylate groups may be cross-linked onto the glycosylated proteins. The types of carbohydrate residues found on glycosylated proteins are shown in FIG. 1.

In another preferred embodiment of the invention, the polypeptide comprises one or more glycosylation motifs. Typical examples of such glycosylation motifs include Asn-X-Ser and Asn-X-Thr, wherein X is any amino acid residue. Polypeptide sequences including these glycosylation motifs may be expressed in eukaryotic hosts, for example, yeast. Methods for expressing polypeptide sequences may be accomplished by standard procedures well known to those skilled in the art.

After glycosylation, therapeutic and/or diagnostic agents may be attached to the carbohydrate residues by standard chemical techniques. The spatial arrangement of the glycosylation motifs is such that there is little or no interference between the therapeutic or diagnostic agents attached thereto.

Therapeutic and Diagnostic Agents

As mentioned above, the polypeptide of the invention has a plurality of therapeutic or diagnostic agents synthetically attached thereto. As used herein, the term "therapeutic agent" refers to any therapeutic agent capable of giving rise to a therapeutic effect, either directly or indirectly.

As used herein, the term "synthetically attached" encompasses straightforward chemical synthetic techniques and also in vivo synthesis using recombinant DNA techniques. The term is not intended to encompass naturally occurring molecules.

By way of example, typical diagnostic agents include fluorescent porphyrins (for use in microscopy or sub-cellular localisation studies [40]), palladium or platinum-based porphyrins (for use in oxygen-sensing applications, or linked to antibodies against relevant biological markers), paramagnetic or radiolabelled porphyrins (for use in imaging studies), or gadolinium-porphyrins (for use as contrast agents).

The therapeutic or diagnostic agent may be attached directly to the polypeptide, or by virtue of a linker group. Direct linkage may occur through any convenient functional group on one of the proteins, such as a hydroxy, carboxy or amino group. Indirect linkage may occur through a linking moiety, for example, those suitable for linking the alpha helix and targeting elements, as described hereinafter in the preparation section.

Preferably, the therapeutic agent is a chemotherapeutic agent or an anti-infectious agent. Examples of chemotherapetuic agents include methotrexate and doxorubicin, whilst examples of anti-infectious agents include metronidazole, nisin, curvacin, netilmicin, amikacin, Microcin B17, rifabutin and sparfloxacin.

In an alternative preferred embodiment, the therapeutic agent is a therapeutic peptide or protein. Typical examples may include peptides that are toxic or corrective, natural or synthetic.

In yet another preferred embodiment, the therapeutic agent is a nucleic acid. Nucleic acids can be attached for the purposes of corrective or destructive cell gene therapy.

The therapeutic agent may also be a boronated porphyrin (for boron capture neutron therapy-BCNT [38].

More preferably, the therapeutic agent is a photosensitising agent. Typical photosensitising agents may include, for example, meta-tetrahydroxyphenyl chorin, 5-aminolaevulanic acid, BPD-benzoporphyrin derivative, meso-tetrahydrophenyl bacteriochlorin, chlorin $e_6$, pyropheophorbide-a, bacteriochlorin-a and sulfonated aluminium phthalocyanine.

By linking novel or established PS agents to small, targetable carrier proteins specifically designed to accept these PS drugs without compromising their function, the invention allows delivery of a highly specific dose of PS drug to a target tissue, which can later be activated by light. These carrier-PS drug conjugates are advantageous over existing targeted and non-targeted PDT approaches in that a greater amount of the PS agent can accumulate in the target tissue, often with tissue to blood/normal organ ratios of 100:1 or better, in shorter time intervals. These agents also have advantages over other targetable strategies as they give rise to lower side effects and result in little or no immunogenicity. The type and number of PS agents attached can be controlled very accurately by engineering the polypeptide molecules, thus obtaining optimal physical and biological characteristics. The fact that the toxic species is generated in the second step means that the agent is not toxic during the delivery step and the toxic species does not have to be released from the polypeptide.

In a particularly preferred embodiment, the polypeptide of the invention is used in combination with one or more inhibitors of one or more oxygen radical scavenging enzymes. The use of such inhibitors effectively increases the availability of reactive oxygen species (ROS) in the target tissue. Inhibitors of this type may be administered consecutively, simultaneously or sequentially with the polypeptide of the invention. Alternatively, said one or more inhibitors may be attached by virtue of a linker moiety to the polypeptide, for example, by attaching to any of the above-mentioned functional amino acid residues. Typical examples of suitable enzyme inhibitors include 3-amino-1,2,4-triazole (catalase inhibitor), taxifolin (glutathione-S-transferase inhibitor), mercaptosuccinate (glutathione peroxidase inhibitor) and 2-methoxyoestradiol (superoxide dismutase inhibitor).

Derivatised therapeutic agents, such as photosensitiser drugs, whose chemical properties are compatible with chemical linking to amine groups, can be attached to the helix using standard chemical techniques. This results in a helix carrying therapeutic agents which are optimally separated so that there is little or no interference between each drug molecule. Such interference may be in the form of chemical quenching, photo-chemical quenching or steric hindrance.

Therapeutic and Diagnostic Applications

A further aspect of the invention relates to the use of a polypeptide as described above in the preparation of a medicament for the prevention and/or treatment of disease. As used herein the phrase "preparation of a medicament" includes the use of a polypeptide of the invention directly as the medicament in addition to its use in a screening programme for the identification of further agents or in any stage of the manufacture of such a medicament. Diseases which may be treated according to the invention include cancer, age-related macular degeneration, microbial infections, arthritis and other immune disorders and cardiovascular disease.

Another aspect relates to a method of treatment comprising administering to a subject in need thereof a therapeutically effective amount of a polypeptide according to the invention.

Likewise, yet another aspect relates to a diagnostic method comprising administering to a subject a diagnostically effective amount of a polypeptide according to the invention.

Yet another aspect of the invention relates to a method of transporting a therapeutic or diagnostic agent into a cell comprising exposing a cell to a polypeptide according to the invention.

Polynucleotide Sequences

Another aspect of the invention provides a polynucleotide sequence encoding all or part of the polypeptide of the invention.

As used herein the term "polynucleotide" refers to a polymeric form of nucleotides of at least 10 bases in length and up to 1,000 bases or even more, either ribonucleotides or deoxyribonucleotides or a modified form of either type of nucleotide. The term includes single and double stranded forms of DNA.

Polynucleotides may be constructed using standard recombinant DNA methodologies. The nucleic acid may be RNA or DNA. Where it is RNA, manipulations may be performed via cDNA intermediates. Reference may be made to Molecular Cloning by Sambrook et al. (Cold Spring Harbor, 1989) or similar standard reference books for exact details of the appropriate techniques.

Sources of nucleic acid may be ascertained by reference to published literature or databanks such as GenBank. Nucleic acid encoding the desired polypeptide sequences may be obtained from academic or commercial sources where such sources are willing to provide the material or by synthesising or cloning the appropriate sequence where only the sequence data are available. Generally this may be done by reference to literature sources which describe the cloning of the gene in question.

Alternatively, where limited sequence data is available or where it is desired to express a nucleic acid homologous or otherwise related to a known nucleic acid, exemplary nucleic acids can be characterised as those nucleotide sequences which hybridise to the nucleic acid sequences known in the art.

It will be understood by a skilled person that numerous different nucleotide sequences can encode the same peptides used in the present invention as a result of the degeneracy of the genetic code. In addition, it is to be understood that skilled person may, using routine techniques, make nucleotide substitutions that do not affect the peptides encoded by the nucleotide sequence of the present invention to reflect the codon usage of any particular host organism in which the peptide of the present invention is to be expressed.

Variants/Homologues/Derivatives

In addition to the specific amino acid sequences and nucleotide sequences mentioned herein, the present invention also encompasses the use of variants, homologues and derivatives thereof. Here, the term "homologue" means an entity having a certain homology with the subject amino acid sequences and the subject nucleotide sequences. Here, the term "homology" can be equated with "identity".

With respect to sequence homology, preferably there is at least 75%, more preferably at least 85%, more preferably at least 90% homology to the reference sequences. More preferably there is at least 95%, more preferably at least 98%, homology. Nucleotide homology comparisons may be conducted using a sequence comparison program such as the GCG Wisconsin Bestfit program.

Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the. default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However, for some applications, it is preferred to use the GCG Bestfit program. A new tool, called BLAST 2 Sequences is also available for comparing protein and nucleotide sequence (see FEMS Microbiol Lett 1999 174(2): 247-50; FEMS Microbiol Lett 1999 177(1): 187-8 and tatiana@ncbi.nlm.nih.gov).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| | | |
|---|---|---|
| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, β-alanine*, L-α-amino butyric acid*, L-γ-amino butyric acid*, L-α-amino isobutyric acid*, L-ε-amino caproic acid#, 7-amino heptanoic acid*, L-methionine sulfone#*, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid# and L-Phe (4-benzyl)*.

The notation * has been utilised for the purpose of the discussion above (relating to homologous or non-homologous substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

The nucleotide sequences for use in the present invention may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in to enhance the in vivo activity or life span of nucleotide sequences of the present invention.

Preparation, Expression Vectors and Host Cells

The polypeptides of the present invention may be prepared by any method known in the art, including recombinant DNA techniques. Alternatively, the polypeptide may be a naturally occurring polypeptide.

The present invention also relates to vectors which comprise a polynucleotide useful in the present invention, host cells which are genetically engineered with vectors of the invention and the production of peptides useful in the present invention by such techniques.

For recombinant production, host cells can be genetically engineered to incorporate expression systems or polynucleotides of the invention. Introduction of a polynucleotide into the host cell can be effected by methods described in many standard laboratory manuals, such as Sambrook et al, such as calcium phosphate or chloride transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as streptococci, staphylococci, *E. coli*, streptomyces and *Bacillus subtilis* cells; fungal cells, such as yeast cells and *Aspergillus* cells; insect cells such as *Drosophila* S2 and *Spodoptera* Sf9 cells; animal cells such as CHO, COS, NSO, HeLa, C127, 3T3, BHK, 293 and Bowes melanoma cells; and plant cells.

A great variety of expression systems can be used to produce a polypeptide useful in the present invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al.

For secretion of the translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and/or purification.

Chemically coupled sequences can be prepared from individual protein sequences and coupled using known chemically coupling techniques. The polypeptide can be assembled using conventional solution- or solid-phase peptide synthesis methods, affording a fully protected precursor with only the terminal amino group in deprotected reactive form. This function can then be reacted directly with a second protein or a suitable reactive derivative thereof. Alternatively, the amino group may be converted into a different functional group suitable for reaction with a second protein. Thus, e.g. reaction of the amino group with succinic anhydride will provide a selectively addressable carboxyl group, while further peptide chain extension with a cysteine derivative will result in a selectively addressable thiol group. Once a suitable selectively addressable functional group has been obtained in the delivery vector precursor, a second protein may be attached through e.g. amide, ester, or disulphide bond formation. Cross-linking reagents which can be utilized are discussed, for example, in Neans, G. E. and Feeney, R. E., *Chemical Modification of Proteins*, Holden-Day, 1974, pp. 39-43.

The present invention also provides a method of preparing a polypeptide as described above, said method comprising conjugating a therapeutic or diagnostic agent to an alpha-helical polypeptide.

In a preferred embodiment, the method further comprise the step of placing the polypeptide so prepared in a container for subsequent therapeutic or diagnostic use.

Preferably, the container has attached thereto a label indicating regulatory approval for said therapeutic or diagnostic application.

Pharmaceutical Compositions

A further aspect of the invention provides a pharmaceutical composition comprising a polypeptide as described hereinbefore and a pharmaceutically acceptable diluent, excipient or carrier (including combinations thereof).

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Examples of suitable carriers include lactose, starch, glucose, methyl cellulose, magnesium stearate, mannitol, sorbitol and the like. Examples of suitable diluents include ethanol, glycerol and water.

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be administered using a minipump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be administered by a number of routes.

Where the composition is to be administered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

BRIEF DESCRIPTION OF THE DRAWINGS

The present invention will now be described by way of example and with reference to the following figures wherein:

FIG. 1 shows the modular structure of the multifunctional targetable-carrier protein of the invention SEQIDNOs 10-14 respectively.

FIG. 2 shows the molecular structure of helical based carrier proteins for therapeutic agents. In more detail, FIGS. 2(A) and (B) show a single peptide α-helix engineered to contain optimally-spaced lysine or arginine residues, which can be used to deliver PS or other drugs. Side (B) and end-on (A) views show favourable spacing of the amino groups used to attach the drugs. FIGS. 2(C) and (D) show a 4-helix bundle, engineered to contain optimally-spaced cysteine residues, which can be used to deliver PS or other drugs. Side (B) and end-on (A) views show favourable spacing of the thiol groups used to attach the drugs.

FIG. 3 shows how a scFv and a 4-helix bundle gene would be assembled in a bacterial expression vector to produce the scFv-helix bundle fusion protein.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA* Methods in Enzymology, Academic Press. Each of these general texts is herein incorporated by reference.

EXAMPLES

Example 1

Figure 3:
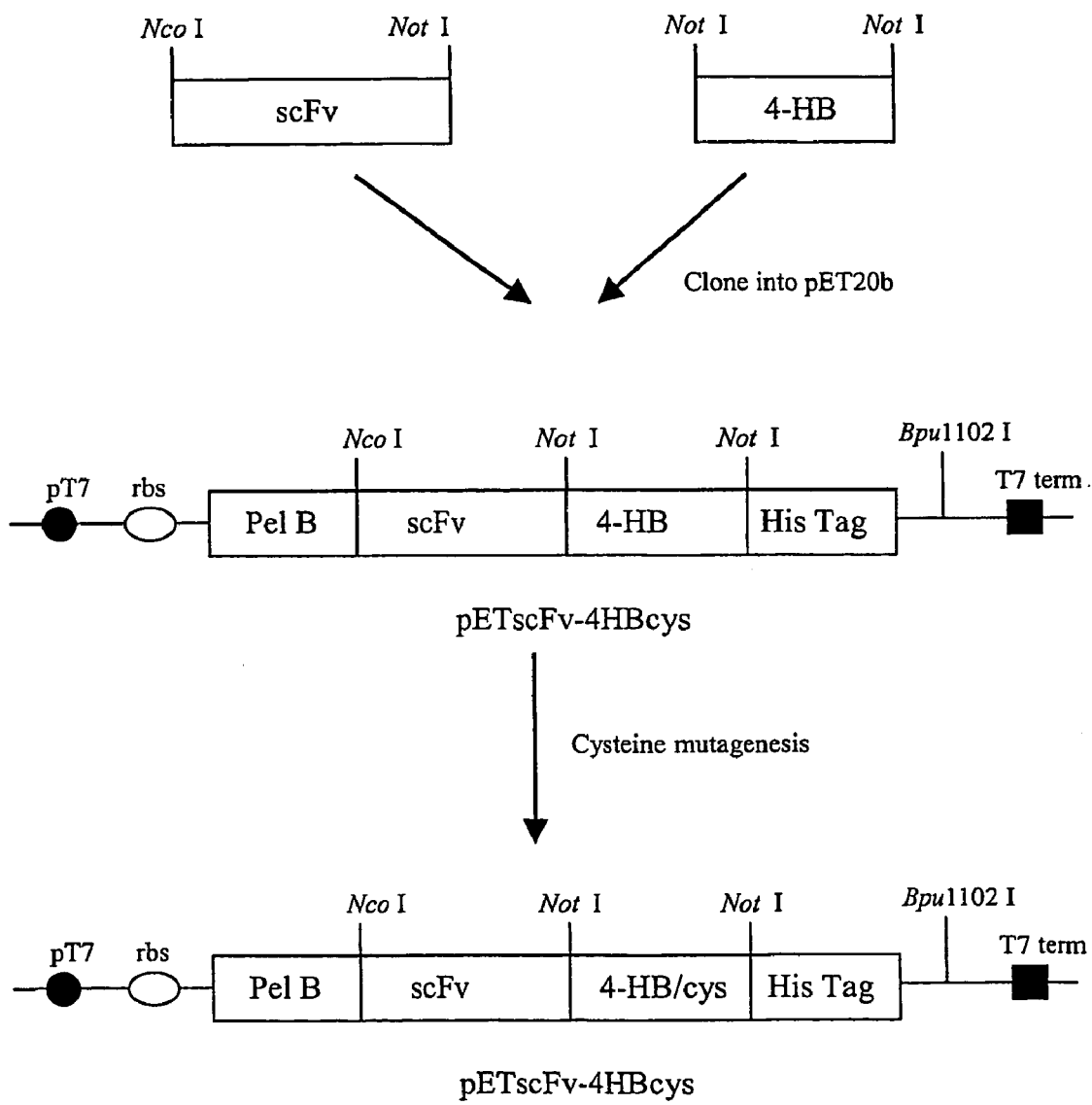
FIG. 3 shows the construction of the scFv-4-helix bundle fusion gene. In more detail.

1.1 Synthesis and Utility of scFv-4 Helix Bundle Fusion Protein Carrying PS Drug Molecules A chosen, well characterised scFv is PCR amplified and cloned as an Nco I/Not I fragment into the bacterial expression vector pET20b (Novagen) to create pETscFv. A DNA cassette containing a 4 helix bundle (e.g. a derivative of the bacterial protein 'rop') is PCR amplified and cloned into the Not I site of pETscFv to create pETscFv4HB (FIG. 3). Appropriate DNA primers are used introduce cysteine residues at optimal positions in the helix bundle and to replace any cysteine residues in the scFv (with residues which do not significantly alter the binding characteristics of the scFv, such as serine, alanine and glycine). The resulting construct is called pETscFv4HBcys The vector pETscFv4HBcys is transformed into *E. coli* BL21(DE3) (Novagen) by the calcium chloride method [41] and plated onto 2TY agar plates containing 100 μg/ml ampicillin [41]. Single colony transformants are picked and re-streaked onto fresh 2TY Agar plates containing amplicillin.

A single colony is picked and grown in 5 ml of 2TY media containing 100 μg/ml ampicillin at 30° C., in a shaking incubator (250 rpm) for 8-16 hr. This culture is then used to inoculate a culture of 500 ml 2TY media containing 100 μg/ml ampicillin and grown under similar conditions for a further 3-16 hr.

The culture supernatant is harvested and concentrated using an Amicon ultrafiltration stirred cell with a 30 KDa cut-off membrane to a final volume of 10 ml. Alternatively, the bacterial periplasm can be prepared using the sucrose osmotic shock method [19] in a volume of 10 ml.

Figure 4:
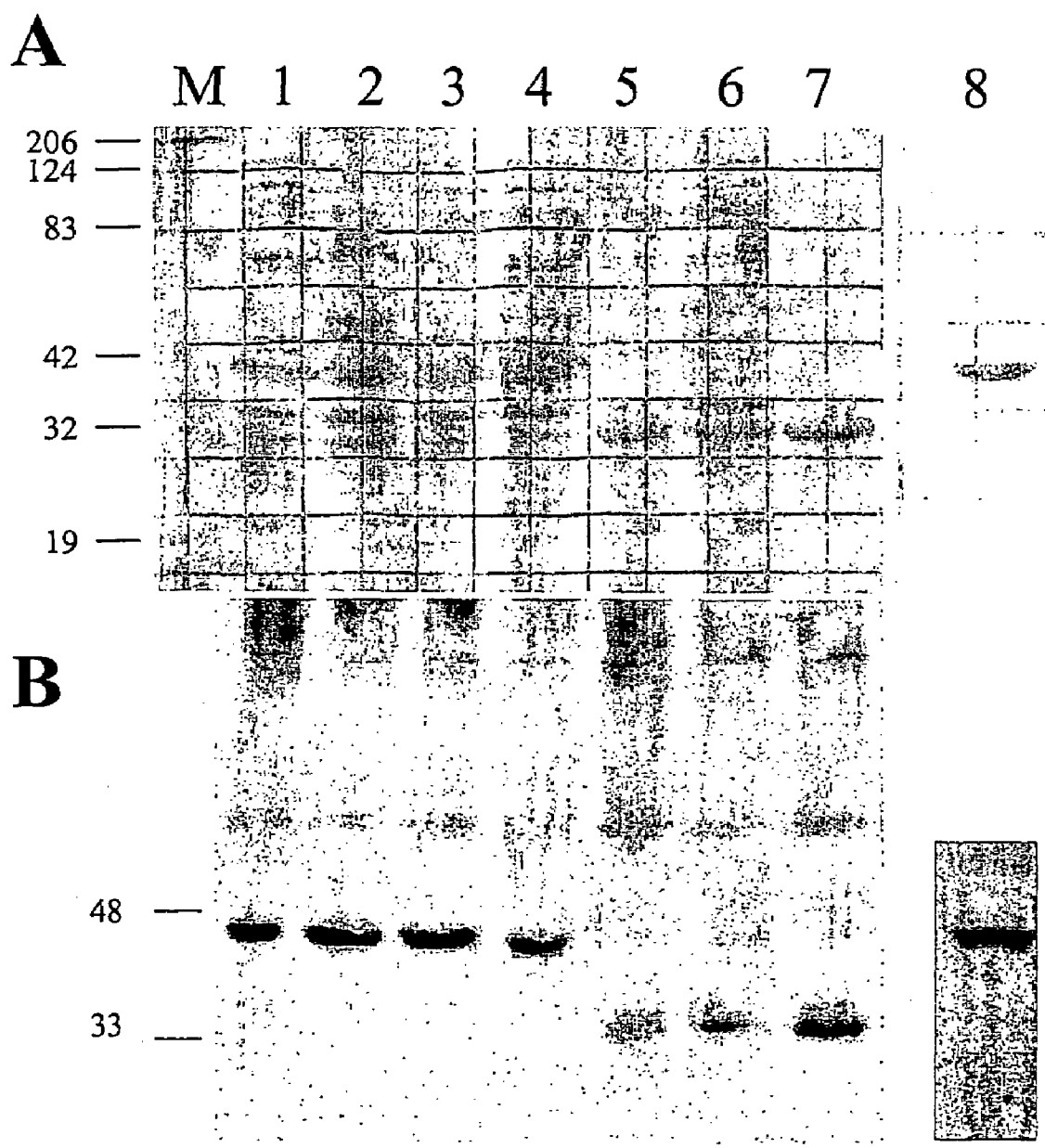
FIG. 4 shows over-expression anti-CEA scFv (lanes 5-7) and scFv-4 helix bundle (lanes 1-4) fusion protein in *E. coli* BL21(DE3). (A) Whole cell lysates are analysed by SDS-PAGE stained with coomassie blue. (B) Whole cell lysates are analysed by western blot using a mouse anti-His tag monoclonal antibody (Qiagen) followed by anti mouse-horseradish peroxidase (Sigma) developed by ECL (Amersham). M-molecular weight markers in KDa. Lane 8 represents substantially pure scFv-4 helix bundle fusion protein after IMAC on Nickel sepharose.

The concentrated supernatant or periplasmic extract is dialysed for 16 hr against 5 L of phosphate-buffered saline (PBS) containing 0.5 M NaCl and 2 mM $MgCl_2$. This is then applied to a copper (II) or nickel (II)-charged chelating sepharose column (Amersham-Pharmacia Biotech) and purified by immobilised metal affinity chromatography (IMAC) for example as described in Deonarain et al [19]. The recombinant fusion protein should elute in an imidazole gradient at between 40 and 150 mM imidazole. The eluted fusion protein is further purified by gel filtration on a superdex-200 column (Amersham-Pharmacia Biotech) equilibrated in PBS. FIG. 4 shows shows data for the expression and purification of the resulting fusion protein, scFv-4-helix bundle-cys.

1.2 Coupling of Porphyrins to scFv-4-helix Bundle-cys

A porphyrin (5-(3-aminophenyl)-10,15,20-triphenylporphyrin is derivatized by reacting with excess bromoacetylbromide (dissolved in acetone containing sodium carbonate) to form (5-(3-bromoacetamidophenyl)-10,15,20-triphenylporphyrin. 10 μmol of the derivatized porphyrin and 10 mg of the scFv-4-helix bundle-cys are dissolved separately in 20 ml of dry dimethyl formamide. These two solutions are added over a period of 3 hours to 50 ml dry dimethyl formamide containing 25 mg sodium carbonate. These reactions are performed in the dark, under argon. The final product is scFv-4-helix bundle-cys with optimally conjugated porphyrins (scFv-4-helix bundle-cys/porphyrin). The scFv-4-helix bundle-cys/porphyrin is dialysed into PBS and concentrated as above.

The number of porphyrins attached to the scFv-4-helix bundle-cys fusion protein is determined using electrospray mass spectrometry, compared to the scFv-4-helix bundle-cys alone. To confirm the position of attachment on the 4-helix bundle, the protein will be fragmented by trypsin digestion and the resulting peptides analysed by mass spectrometry.

1.3 Photophysical Studies

The photophysical characteristics of the scFv-4-helix bundle-cys/porphyrin are measured and compared to the free porphyrin. This includes UV/Visible absorption spectrum, fluorescence spectrum, fluorescence decay times, triplet state spectrum, singlet oxygen yield and quenching experiments of triplet state by substrates.

1.4 Binding Studies

In vitro binding characteristics of the scFv-4-helix bundle-cys/porphyrin molecule are carried out by ELISA [42] or by BIACore surface plasmon resonance using published methods, compared to the unmodified scFv and scFv-4-helix bundle. Cell binding of the scFv-4-helix bundle-cys/porphyrin can also be compared to the unmodified proteins can be determined by Fluorescently Activated Cell Sorting (FACS), confocal fluorescence microscopy.

1.5 Cytotoxicity Studies

In vitro cell cytotoxicity is measured as follows: The target cells (in this example, an antigen positive cell line such as MCF7) are seeded at a concentration of $1\times10^4$ cells per well in a 96-well microtitre plate in DMEM media/10% FCS. Cells are allowed to grow overnight in a humidified incubator at 37° C., with 5% $CO_2$. The next day, concentrations scFv-4-helix bundle-cys/porphyrin ranging from 1 μM to 1 nM are added to the wells in triplicate. After 3-6 hours, the media is washed 3 times in complete media and the cells are exposed to light from a 500 W halogen lamp for 10-20 min. The total light dose is about 25-50 $J/cm^2$. The following day, cell death is measured by lactase dehydrogenase release (Cytotox-96 kit, Promega). These experiments are done on an antigen cell line (e.g. KB cells). The molecules tested are the unmodified scFv, the scFv-4-helix bundle, free porphyrin and scFv-4-helix bundle-cys/porphyrin.

In vivo tumour eradication can be demonstrated as follows: Approx $1\times10^6$ MCF7 cells are injected s.c. into the flank of a nude BALB/C mouse and tumours are allowed to establish for 1-2 weeks. 50-500 μg of scFv-4-helix bundle-cys/porphyrin is injected intravenously into the tail vein of tumour-bearing mice and allowed to accumulate in the tumour over a period of 12-36 hrs. At a time when the tumour:normal organ ratio is high (10:1 or better), light is irradiated onto the tumours. The size of the tumours is measured using callipers and compared to mice carrying antigen-negative tumours, and in animals injected with scFv alone, scFv-4-helix bundle, free porphyrin and scFv-4-helix bundle-cys/porphyrin.

Example 2

2.1 Preparation of pETscFv4HBLys

A scFv-4 helix bundle was prepared in accordance with the methodology described in Example 1 and FIGS. 1 to 3, except that appropriate primers were used to introduce lysine residues at optimal positions in the helix bundle. The resulting construct is called pETscFv4HBLys. An scFv which targets CEA (carcinoembryonic antigen) was used.

FIG. 4 shows the expression of four such clones in *E. coli* BL21(DE3) compared with the scFv (against CEA) alone. The expression is generally good with yields of pure protein of approx. 1 mg/L cell culture.

2.2 Coupling of Chlorin $e_6$ to scFv4-helix Bundle-Lys

The N-hydroxysuccinimide (NHS) ester of the photosensitiser chlorin $e_6$, was prepared by reacting 1.5 equivalents of dicyclohexylcarbodiimide and 1.5 equivalents of NHS with one equivalent of chlorin $e_6$ in dry dimethyl sulphoxide (DMSO). The reaction was carried out under an inert gas (e.g. argon) and in the dark at room temperature and was complete in 2 hours, (tlc: silica gel 3% methanol in chloroform). A similar procedure can be used to prepare the active esters of other carboxyl containing photosensitisers.

N-ethylmorpholine (1 μl), DMSO (10 ml) and the scFv-4 helix bundle (100 μg in approx. 1 ml of PBS buffer) were stirred together under nitrogen at room temperature. To this solution was added the DMSO solution containing the photosensitiser-NHS ester. The solution was stirred at room temperature in the dark for 12 hours to synthesise the bundle chlorin $e_6$ conjugate. The conjugate was then dialysed against 2×5 L of PBS. All procedures were carried out in the dark.

Figure 5:
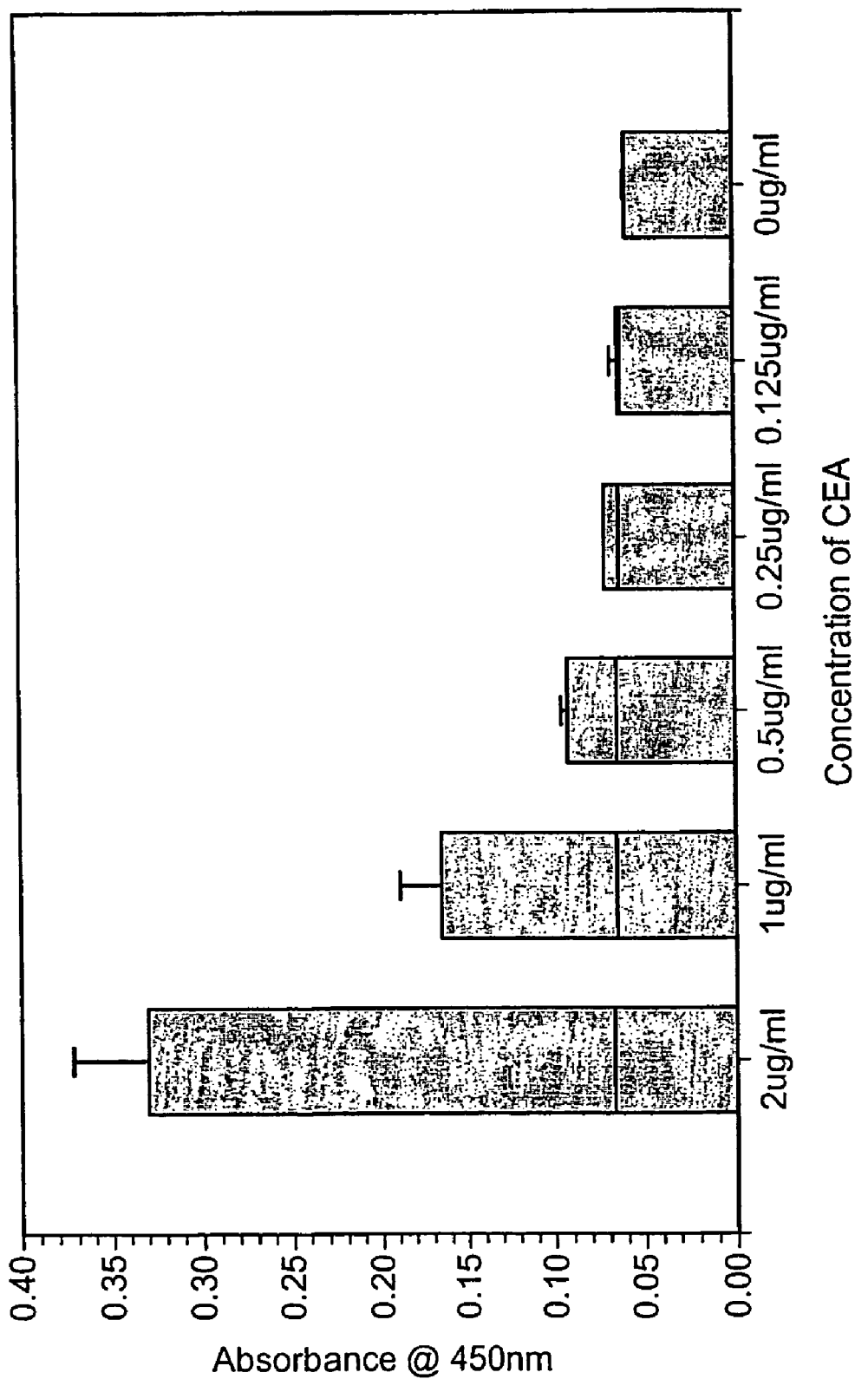
FIG. 5 shows antigen binding ELISA of scFv-4 helix bundle. In more detail, a dilution series of scFv-4 helix bundle coupled to chlorin $e_6$ is added to CEA immobilised on a microtitre plate and binding is visualised using a mouse anti-His tag monoclonal antibody (Qiagen) followed by anti mouse-horseradish peroxidase (Sigma) developed using o-phenyldiamine (OPD) substrate.
Figure 6:
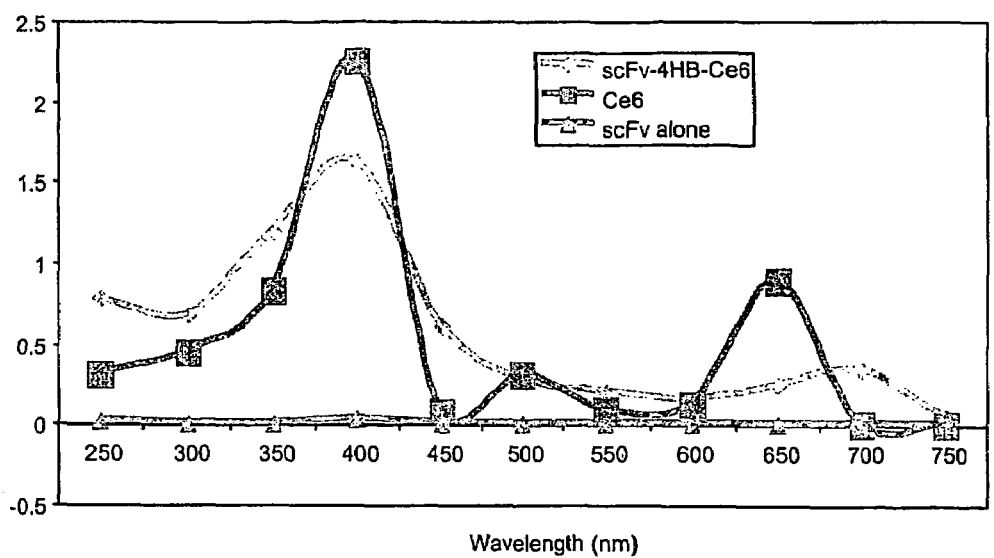
FIG. 6 shows the absorbance spectrum of a scFv-4 helix bundle fusion protein coupled to chlorin $e_6$ sensitiser, compared to free sensitiser. The spectrum was measured using a UV-Vis spectrometer in a 1 cm cuvette.
Figure 7:
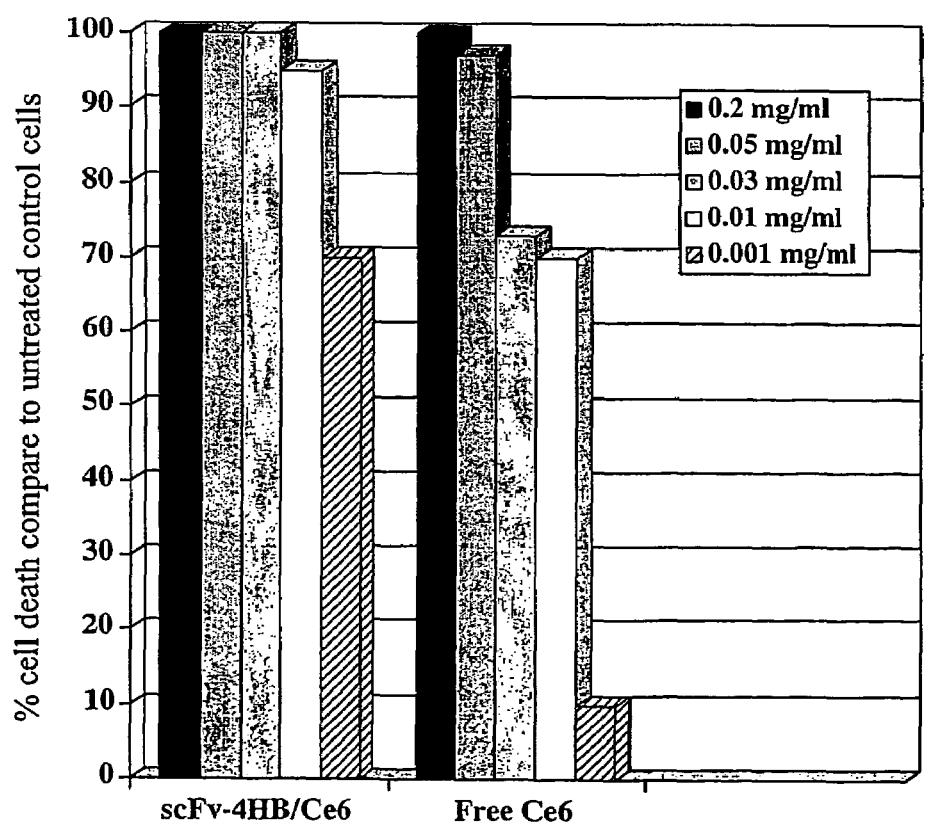
FIG. 7 shows cell killing activity of a scFv-4 helix bundle fusion protein coupled to clorin $e_6$ sensitiser. Cell killing was analysed on CEA-antigen positive cells (LS174T). Various concentrations of scFv-4 helix bundle fusion protein-chlorin $e_6$ conjugate and free chlorin $e_6$ was added and cell cytotoxicity was measured after 2 hours binding and exposure to light. The light energy dose was 2J using an LED source of 600-700 nm. Cell death was measured using the Cytotox-96 kit (Promega). Preliminary results indicate that the targeted PDT is about 10-fold more effective than the free sensitiser.

FIG. 5 shows target binding data for the chlorin $e_6$-scFv4-helix bundle-Lys conjugate, as measured by the technique described above in paragraph 1.4. FIG. 6 shows photophysical data for the resulting chlorin $e_6$-scFv4-helix bundle-Lys conjugate measured in accordance with paragraph 1.3 above. FIG. 7 shows cell killing activity using cell line LS174T, as measured by the technique described above in paragraph 1.5.

Various modifications and variations of the described methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

REFERENCES

[1] Price & Sikora (eds). Treatment of Cancer. Chapman & Hall 1995

[2] Press, O W & Rasey, J (2000). Semin Oncol. 6, 62-73. Principles of Radioimmunotherapy for hematologists and oncologists.

[3] Affleck, K et al (1992). Br. J. Cancer 65, 838-844. Monoclonal antibody targeting of methotrexate (MTX) against MTX-resistant tumour cell lines.

[4] Beers R et al. (2000). Clin Cancer Res. 6, 2835-43. Immunotoxins with increased activity against epidermal growth factor receptor vIII-expressing cells produced by antibody phage display.

[5] Rosenkranz, A. A et al (2000). Immunol. And Cell Biol. 78, 452-64. Targeted intracellular delivery of photosensitizers to enhance photodynamic therapy.

[6] Hudson P J. (2000). Expert Opin Investig Drugs 9, 1231-42. Recombinant antibodies: a novel approach to cancer diagnosis and therapy.

[7] Kuby (2000). Immunology, 4th Ed. W. H. Freeman.
[8] Hoogenboom H R, & Chames P (2000). Immunol Today. 21, 371-8. Natural and designer binding sites made by phage display technology.
[9] Glennie, M J & Johnson, W M (2000). Immunol. Today 21, 403-410. Clinical trials of antibody therapy.
[10] Hird, V. et al. (1994). Br. J. Cancer 68, 403-6. Adjuvant therapy of ovarian cancer with radioactive monoclonal antibody.
[11] Begent, R H et al. (1996). Nat. Med. 2, 979-84. Clinical evidence of efficient tumor targeting based on single-chain Fv antibody selected from a combinatorial library.
[12] Rowlinson-Busza, G. et al. (1996). Tumour Targeting 2, 37-48. Comparison of intact monoclonal antibody, its F(ab)2 and Fab fragments and recombinant single-chain Fv in human tumour xenograft model.
[13] Boxer G M et al. (1994). Br. J. Cancer 69, 307-14. Localisation of monoclonal antibodies reacting with different epitopes on carcinoembryonic antigen (CEA)—implications for targeted therapy.
[14] Little, M. et al (2000). Immunol. Today 21, 364-370. Of mice and men: hybridoma and recombinant antibodies.
[15] Verhaar M J et al. (1995). Int J Cancer 61, 497-501. A single chain Fv derived from a filamentous phage library has distinct tumor targeting advantages over one derived from a hybridoma.
[16] Epenetos, A. A. et al (1986). Cancer Res. 46, 3183-91. Limitations of radiolabeled monoclonal antibodies for localization of human neoplasms.
[17] Gangopadhyay, A etal; (1996). Nucl. Med. Biol. 23, 257-61. Modification of antibody isoelectric point affects biodistribution of 111-indium-labeled antibody.
[18] Chen S Y et al. (1995). Gene Ther. 2, 116-23. Design of a genetic immunotoxin to eliminate toxin immunogenicity.
[19] Deonarain M P & Epenetos A A (1998) Br. J. Cancer. 77, 537-46. Design, characterization and anti-tumour cytotoxicity of a panel of recombinant, mammalian ribonuclease-based immunotoxins.
[20] Pouton, C W (1998). Adv Drug Del. Rev. 34, 51-64. Nuclear import of polypeptides, polynicleotides and supramolecular complexes.
[21] Zhang, F. et al. 912000). FEBS Letts 478, 89-94. M-ABC2, a new human mitochondrial ATP-binding cassette membrane protein.
[22] Blagoveshchenskaya, A D et al. (1998). J. Biol. Chem. 273, 27896-903. A balance of opposing signals within the cytoplasmic tail controls the lysosomal targeting of P-selectin.
[23] Pelham H R (1995). Curr Opin Cell Biol. 7, 530-5. Sorting and retrieval between the endoplasmic reticulum and Golgi apparatus.
[24] Plank, C. et al. (1998). Adv Drug Del. Rev. 34, 21-35. Application of membrane-active peptides for drug and gene delivery across cellular membranes.
[25] Ghettie, V. & Vitetta, E. (1994) *Pharmacol. Ther.* 63, 209-34. Immunotoxins in the therapy of cancer: from bench to clinic.
[26] Linardou, H. et al. (2000) Int . J. Cancer 86, 561-569. A recombinant cytotoxic chimera based on mammalian deoxyribonuclease-I.
[27] Hopper, C. (2000). Lancet Oncology 1, 212-219. Photodynamic therapy: a clinical reality in the treatment of cancer.
[28] Polo, L. et al. (1992). Cancer Letts 66, 217-23. The distribution of the tumour photosensitizers Zn(II)-phthalocyanine and Sn (IV)-etiopurpurin among rabbit plasma proteins.
[29] Pervaiz S. (2001). FASEB J.15, 612-7. Reactive oxygen-dependent production of novel photochemotherapeutic agents.
[30] Dellinger, M et al. (1996). Photochem. Photobiol. 64, 182-7. Apoptosis or necrosis following Photfrin photosensitization: Influence of the incubation protocol.
[31] Schmidt-Erfurth U. et al. (1999). Arch. Ophthalmol. 117, 1329-1345. Treatment of Age-related Macular degeneration with photodynamic therapy (TAP) study group. Photodynamic therapy of subfoveal neovascularization in age-related macular degeneration with verteporfin.
[32] Ahmad, N. et al (1998). PNAS USA 95, 6977-6982. Photodynamic therapy results in induction of WAF1/CIP1/P21 leading to cell cycle arrest and apoptosis.
[33] Fiers, W. et al. (1998). Oncogene 18, 7719-7730. More than one way to die: apoptosis, necrosis and reactive oxygen species.
[34] Milgrom, L R & O'Neill, F (1995). Tetrahedron Letts. 51, 2137-44. Towards synthetic-porphyrin/monoclonal antibody conjugates.
[35] Akhlynina, T V et al. (1997). J. Biol. Chem. 272, 20328-20331. Nuclear targeting of chlorin $e_6$ enhances its photosensitizing activity.
[36] Vrouenraets, M B et al. (1999). Cancer Res. 59, 1505-1513. Development of meta-tetrahydroxypheneylchlorin-monoclonal antibody conjugates for photoimmunotherapy.
[37] Vrouenraets, M B et al. (2000). Int. J. Cancer 88, 108-114. Targeting of a hydrophilic photosensitizer by use of internalizing monoclonal antibodies: A new possibility for use in photodynamic therapy.
[38] Hill, J S et al. (1995). PNAS (USA) 92, 12126-12130. Selective tumour kill of cerebral glioma by photodynamic therapy using a boronated porphyrin photosensitizer.
[39] Devanathan, S et al. (1990). PNAS (USA) 87, 2980-2984. Readily available fluorescin isothiocyanate-conjugated antibodies can easily be converted into targeted phototoxic agents for antibacterial, antiviral and anticancer therapy.
[40] Inaguma M & Hashimoto K. (1999). Cancer 86, 2201-11. Porphyrin-like fluorescence in oral cancer: In vivo fluorescence spectral characterization of lesions by use of a near-ultraviolet excited autofluorescence diagnosis system and separation of fluorescent extracts by capillary electrophoresis.
[41] Sambrook et al. (1989). DNA Cloning. A Laboratory Manual. Cold Spring Harbor.
[42] Harlow, E. & Lane, D. (1999). Using Antibodies. A Laboratory Manual. Cold Spring Harbor.

TABLE 1

Therapeutic uses of Antibodies [29]

| Antibody | Target | Application |
| --- | --- | --- |
| Herceptin | ErbB2 (Her 2) receptor | Breast cancer therapy |
| Rituxan | CD20 | Lymphoma |
| Theragyn (Pemtumomab) | Muc-1 | Ovarian cancer [30] |
| Infliximab | TNFα | Rheumatoid arthritis, Crohn's disease |
| Zenapax | CD25 | Allograft rejection |
| Panorex | 17-1A surface antigen | Colorectal cancer |
| Vitaxin | αVβ3 intergrin | Sarcoma |
| Protovir | Cytomegalovirus (CMV) | CMV infection |
| MFE-23 | Carcinoembryonic antigen | Colorectal cancer [31] |

TABLE 2

Peptide sequences which could be used for sub-cellular localisation

| Name of Sequence | Function | Amino Acid Sequence [ref.] |
|---|---|---|
| SV 40 large T nuclear localisation | Targets polypeptides to the nucleus | KKKKRPR (SEQIDNO:1) [20] |
| Human SRY | Targets polypeptides to the nucleus | KRPMNAFIVWSRDQRRK (SEQIDNO:2) [20] |
| ATP-binding protein N-terminal peptide containing mitochondria targeting | Targets polypeptides to the mitochondria | MLVHLFRVGIRGGPFPGRL LPPLRFQTFSAVRYSDGYR SSSLLRAVAHLPSQLWA (SEQIDNO:3) [21] |
| Lysosomal membrane targeting | Targets polypeptides to the lysosomes | KCPL (SEQIDNO:4) [22] |
| Endoplasmic reticulum (ER) Retention Signal | Allows proteins to traffic back to the ER | KDEL (SEQIDNO:5) [23] |
| Influenza Haemaglutinin HA2 | Disrupts membrane | GLFGAIAGFIENGWEGMID GWYG (SEQIDNO:6) [24] |
| Polio virus vp1 | Disrupts membrane | GIEDLISEVAQGALTLVP (SEQIDNO:7) [24] |
| Human defensin | Disrupts membrane | ACYCRIPACIAGERRYGTCI YQGRLWAFCC (SEQIDNO:8) [24] |
| Sendai virus fusion protein F1 | Disrupts membrane | FFGAVIGTIALGVATSAQIT AGIALAEAR (SEQIDNO:9) [24] |

TABLE 3

Clinical Results with PDT in cancer [27]

| Disease | Photosensitiser | Result |
|---|---|---|
| Barrett's mucosal cancer | Porfimer sodium | 75% conversion to normal epithelium and tumours eliminated |
| Barrett's oesophagus cancer | Systemic ALA | High-grade dysplasia eradicated in all patients |
| Bladder cancer | Hematoporphyrin derivative | 74% complete response, 30% alive after 5 years |
| Basal cell cancer of skin | Topical ALA | 90% complete response |
| Oral cancer | Dihematoporphyrin ether | 87% complete response over 5-53 months |
| Chest wall recurrence in breast cancer | Dihematoporphyrin ether | 20% complete response, 45% partial response |

The invention claimed is:

1. A polypeptide comprising a mutant form of 'rop' (repressor of primer) having four alpha-helices having synthetically attached thereto a plurality of therapeutic or diagnostic moieties, and further comprising a targeting element,
wherein at least one alpha-helix of the four alpha-helices is a 19-residue helix having functional amino acids conjugated to said therapeutic agents or diagnostic moieties at positions 2, 8, 10, 14, and 16, wherein the functional amino d1 acids are independently selected from the group consisting of lysine and cysteine, and said therapeutic agents or diagnostic moieties may be the same or different, and
wherein said targeting element is selected from a recombinant antibody, a Fab fragment, a F(ab')2 fragment, a single chain Fv, a diabody, a disulfide linked Fv, a single antibody domain and a CDR.

2. A polypeptide according to claim 1 wherein said targeting element further comprises a synthetic or natural peptide, a growth factor, a hormone, a peptide ligand, a carbohydrate or a lipid.

3. A polypeptide according to claim 1 which further comprises one or more additional amino acid sequences selected from a sub-cellular targeting peptide and a membrane active peptide.

4. A polypeptide according to claim 3 wherein said sub-cellular targeting peptide targets the nucleus and comprises a sequence selected from KKKKRPR (SEQ ID NO.: 1) and KRPMNAFIVWSRDQRRK (SEQ ID NO: 2).

5. A polypeptide according to claim 3 wherein said sub-cellular targeting peptide targets the mitochondria and comprises the sequence MLVHLFRVGIRGGPFP GRLLPPLR-FQTFSAVRYSDGYRSSSLLRAVAHLPSQLWA (SEQ ID NO: 3).

6. A polypeptide according to claim 3 wherein said sub-cellular targeting peptide targets lysosomes and comprises the sequence KCPL (SEQ ID NO:4).

7. A polypeptide according to claim 3 wherein said sub-cellular targeting peptide allows proteins to traffic back to the endoplasmic reticulum and comprises the sequence KDEL (SEQ ID NO: 5).

8. A polypeptide according to claim 3 wherein said membrane active peptide targets the membrane and comprises a sequence selected from the following:

(i)   GLFGAIAGFIENGWEGMIDGWYG;         (SEQ ID NO:6)

(ii)  GIEDLISEVAQGALTLVP;              (SEQ ID NO:7)

(iii) ACYCRIPACIAGERRYGTCIYQGRLWAFCC;  (SEQ ID NO:8)
      and (iv)  FFGAVIGTIALGVATSAQITAGIALAEAR.   (SEQ ID NO:9)

9. A polypeptide according to claim 1 wherein said therapeutic agent is a chemotherapeutic agent or an anti-infectious agent.

10. A polypeptide according to claim 1 wherein said therapeutic agent is a photosensitising agent.

11. A polypeptide according to claim 10 wherein said photosensitising agent is selected from meta-tetrahydroxyphenyl chlorin, 5-aminolaevulinic acid, BPD-benzoporphyrin derivative, meso-tetrahydrophenyl bacteriochlorin, chlorin $e_6$, pyropheophorbide-a, bacteriochlorin-a and sulfonated aluminium phthalocyanine.

12. A polypeptide according to claim 1 wherein said therapeutic agent is a therapeutic peptide or protein.

13. A polypeptide according claim 1 wherein said therapeutic agent is a nucleic acid.

14. A pharmaceutical composition comprising a polypeptide according to claim 1 and a pharmaceutically acceptable diluent, excipient or carrier.

15. A method of treatment comprising administering to a subject in need thereof a therapeutically effective amount of a polypeptide according to claim 1.

16. A diagnostic method comprising administering to a subject a diagnostically effective amount of a polypeptide according to claim 1.

17. A method of preparing a polypeptide according to claim 1, said method comprising conjugating a therapeutic or diagnostic agent to the functional amino acids on the 19-residue helix.

18. A method according to claim 17 which further comprise the step of placing the polypeptide so prepared in a container for subsequent therapeutic or diagnostic use.

19. A method according to claim 18 wherein said container has attached thereto a label indicating regulatory approval for said therapeutic or diagnostic application.

20. A polypeptide according to claim 1, wherein the mutant form of 'rop' has at least 90% sequence identity compared to a wild-type 'rop'.

21. A polypeptide comprising a mutant form of 'rop' (repressor of primer) having four alpha-helices and a targeting element,
wherein at least one alpha-helix of the four alpha-helices is a 19-residue helix having functional amino acids conjugated to a photosensitising agent at positions 2, 8, 10, 14, and 16, wherein the functional amino acids are independently selected from the group consisting of lysine and cysteine, and
wherein said targeting element is selected from the group consisting of a recombinant antibody, a Fab fragment, a F(ab')$_2$ fragment, a single chain Fv, a diabody, a disulfide linked Fv, a single antibody domain and a CDR.

22. The polypeptide of claim 21, wherein the photosensitising agent is selected from the group consisting of meta-tetrahydroxyphenyl chlorin, 5-aminolaevulanic acid, BPD-benzoporphyrin derivative, meso-tetrahydrophenyl bacteriochlorin, chlorin $e_6$, pyropheophorbide-a, bacteriochlorin-a and sulfonated aluminium phthalocyanine.

23. A polypeptide comprising a mutant form of 'rop' (repressor of primer) having four alpha-helices and a single chain Fv targeting element,
wherein at least one alpha-helix of the four alpha-helices is a 19-residue helix having functional amino acids conjugated to chlorin $e_6$ at positions 2, 8, 10, 14, and 16, and wherein the functional amino acids are independently selected from the group consisting of lysine and cystelne.

24. A polypeptide comprising a mutant form of 'rop' (repressor of primer) having four alpha-helices and a single chain Fv targeting element,
wherein at least one alpha-helix of the four alpha-helices is a 19-residue helix having functional amino acids conjugated to chlorin $e_6$ at positions 2, 8, 10, 14, and 16, wherein the functional amino acids are independently selected from the group consisting of lysine and cysteine, and the mutant form of 'rop' has at least 90% sequence identity compared to a wild-type 'rop'.

* * * * *